(12) United States Patent
Wong et al.

(10) Patent No.: US 11,414,694 B2
(45) Date of Patent: Aug. 16, 2022

(54) NUCLEIC ACID NANOSWITCH CATENANES

(71) Applicants: Children's Medical Center Corporation, Boston, MA (US); Dana-Farber Cancer Institute, Inc., Boston, MA (US)

(72) Inventors: Wesley Philip Wong, Cambridge, MA (US); William M. Shih, Cambridge, MA (US)

(73) Assignees: Children's Medical Center Corporation, Boston, MA (US); Dana-Farber Cancer Institute, Inc., Boston, MA (US)

( * ) Notice: Subject to any disclaimer, the term of this patent is extended or adjusted under 35 U.S.C. 154(b) by 953 days.

(21) Appl. No.: 16/083,932

(22) PCT Filed: Mar. 9, 2017

(86) PCT No.: PCT/US2017/021562
§ 371 (c)(1),
(2) Date: Sep. 11, 2018

(87) PCT Pub. No.: WO2017/156264
PCT Pub. Date: Sep. 14, 2017

(65) Prior Publication Data
US 2020/0308625 A1 Oct. 1, 2020

Related U.S. Application Data

(60) Provisional application No. 62/306,764, filed on Mar. 11, 2016.

(51) Int. Cl.
*C12P 19/34* (2006.01)
*C12Q 1/6804* (2018.01)
(Continued)

(52) U.S. Cl.
CPC ............ *C12Q 1/6804* (2013.01); *B82Y 15/00* (2013.01); *C12Q 1/6813* (2013.01);
(Continued)

(58) Field of Classification Search
CPC ............................ C12Q 1/6813; C12Q 1/6844
See application file for complete search history.

(56) References Cited

U.S. PATENT DOCUMENTS 5,591,601 A   1/1997   Wagner et al.
5,846,949 A   12/1998  Wagner et al.
(Continued)

FOREIGN PATENT DOCUMENTS

JP   2002-114797 A   4/2002
JP   2003-522524 A   7/2003
(Continued)

OTHER PUBLICATIONS

Bikram et al., Biodegradable Poly(ethylene glycol)-co-poly(l-lysine)-g-histidine Multiblock Copolymers for Nonviral Gene Delivery. Macromolecules. Feb. 11, 2004;37(5):1903-16.
(Continued)

*Primary Examiner* — Kenneth R Horlick
(74) *Attorney, Agent, or Firm* — Wolf, Greenfield & Sacks, P.C.

(57) ABSTRACT

The present disclosure provides nucleic acid-based nanoswitch catenanes and methods of use. A nanoswitch catenane may include a single-stranded nucleic acid comprising a first and second terminal domain linked to each other to form a host ring by one of a first, second or third switchable bridges, wherein the first switchable bridge is formed in the presence of a reaction agent through the reaction of two cognate functional groups, each linked to a terminal domain of the single-stranded nucleic acid, wherein the second switchable bridge is formed in the presence of a biomolecule
(Continued)

of interest through binding of the bio-molecule of interest to two cognate antibodies, each linked to a terminal domain of the single stranded nucleic acid, and wherein the third switchable bridge is a link between two cognate functional groups that breaks in the presence of a dissociation agent. A nanoswitch catenane may also include a circular nucleic acid guest ring catenated with the host ring.

24 Claims, 3 Drawing Sheets

(51) Int. Cl.
 B82Y 15/00 (2011.01)
 C12Q 1/6813 (2018.01)
 C12Q 1/6844 (2018.01)
 B82Y 5/00 (2011.01)
(52) U.S. Cl.
 CPC .............. C12Q 1/6844 (2013.01); B82Y 5/00 (2013.01); C12Q 2525/203 (2013.01); C12Q 2537/1373 (2013.01); C12Q 2563/131 (2013.01); C12Q 2563/155 (2013.01)

(56) References Cited

U.S. PATENT DOCUMENTS

| | | | |
|---|---|---|---|
| 6,355,247 | B1 | 3/2002 | Selby et al. |
| 7,842,793 | B2 | 11/2010 | Rothemund |
| 8,501,923 | B2 | 8/2013 | Rothemund |
| 11,254,972 | B2 | 2/2022 | Minev et al. |
| 2005/0112578 | A1 | 5/2005 | Matsuura et al. |
| 2007/0117109 | A1 | 5/2007 | Rothemund |
| 2011/0033706 | A1 | 2/2011 | Krishnan |
| 2011/0243910 | A1 | 10/2011 | Hahn et al. |
| 2011/0293698 | A1 | 12/2011 | Primiano et al. |
| 2012/0263783 | A1 | 10/2012 | Messmer |
| 2013/0136925 | A1 | 5/2013 | Kim et al. |
| 2013/0245102 | A1 | 9/2013 | Ryan et al. |
| 2014/0220655 | A1 | 8/2014 | Sun et al. |
| 2014/0255939 | A1 | 9/2014 | Wong et al. |
| 2016/0271268 | A1 | 9/2016 | Shih et al. |
| 2018/0363022 | A1* | 12/2018 | Li .................. C12Q 1/6806 |
| 2019/0203277 | A1 | 7/2019 | Minev et al. |

FOREIGN PATENT DOCUMENTS

| | | |
|---|---|---|
| JP | 2008-504846 A | 2/2008 |
| JP | 2008-523061 A | 7/2008 |
| JP | 2009-518008 A | 5/2009 |
| JP | 2009-213390 A | 9/2009 |
| JP | 2012-509983 A | 4/2012 |
| WO | WO 2012/058488 A2 | 5/2012 |
| WO | WO 2012/151328 A2 | 11/2012 |
| WO | WO 2014/018675 A1 | 1/2014 |
| WO | WO 2015/070080 A2 | 5/2015 |
| WO | WO 2015/130805 A1 | 9/2015 |
| WO | WO 2015/165643 A1 | 11/2015 |
| WO | WO 2016/144755 A1 | 9/2016 |
| WO | WO 2017/156252 A1 | 9/2017 |
| WO | WO 2018/026880 A2 | 2/2018 |

OTHER PUBLICATIONS

Fujigaya et al., Enhanced cell uptake via non-covalent decollation of a single-walled carbon nanotube-DNA hybrid with polyethylene glycol-grafted poly(l-lysine) labeled with an Alexa-dye and its efficient uptake in a cancer cell. Nanoscale. Oct. 5, 2011;3(10):4352-8. doi: 10.1039/c1nr10635j. Epub Sep. 20, 2011.
Kadlecova et al., Hyperbranched polylysine: a versatile, biodegradable transfection agent for the production of recombinant proteins by transient gene expression and the transfection of primary cells. Macromol Biosci. Jun. 2012;12(6):794-804. doi: 10.1002/mabi.201100519. Epub Apr. 11, 2012.
Rajendran et al., Single-molecule analysis using DNA origami. Angew Chem Int Ed Engl. Jan. 23, 2012;51(4):874-90. doi: 10.1002/anie.201102113. Epub Nov. 25, 2011.
Santos et al., Low-cost fabrication technologies for nanostructures: state-of-the-art and potential. Nanotechnology. Jan. 30, 2015;26(4):042001(1-20). doi: 10.1088/0957-4484/26/4/042001. Epub Jan. 8, 2015.
Schlichthaerle et al., DNA nanotechnology and fluorescence applications. Curr Opin Biotechnol. Jun. 2016;39:41-47. doi: 10.1016/j.copbio.2015.12.014. Epub Jan. 13, 2016.
Babic et al. Poly L-lysine-modified iron oxide nanoparticle for stem cell labelling. Bioconjug Chem. 2008;19:740-50. Epub Feb. 21, 2008.
Dietz et al., Folding DNA into twisted and curved nanoscale shapes. Science. Aug. 7, 2009;325(5941):725-30.
Ding et al., Gold nanoparticle self-similar chain structure organized by DNA origami. J Am Chem Soc. 2010;132(10):3248-9. Epub Feb. 17, 2010.
Douglas et al., Self-assembly of DNA into nanoscale three-dimensional shapes. Nature. May 21, 2009;459(7245):414-8. Author Manuscript, 11 pages.
Hansen et al., Nanoswitch-linked immunosorbent assay (NLISA) for fast, sensitive, and specific protein detection. PNAS. Sep. 26, 2017;114(39):10367-10372. Supporting Information, 4 pages.
Koussa et al., DNA nanoswitches: A quantitative platform for gel-based biomolecular interaction analysis. Nat Methods. Feb. 2015;12(2):123-6. Epub Dec. 8, 2014.
Koussa et al., Protocol for sortase—mediated construction of DNA-protein hybrids and functional nanostructures. Nat Methods. May 2014;67(2):134-41.
Kuzuya et al., Precisely programmed and robust 2D streptavidin nanoarrays by using periodical nanometer-scale wells embedded in DNA origami assembly. Chembiochem. Jul. 2009;10(11):1811-5.
Kuzyk et al., DNA-based self-assembly of chiral plasmonic nanostructures with tailored optical response. Nature. Mar. 15, 2012;483(7389):311-4. doi:10.1038/nature10889.
Kwoh et al., Stablilization of poly-L-lysine/DNA polyplexes for in vivo gene delivery to the liver. Biochimica et Biophysica Acta. 1999;1444:171-90.
Lu et al., Recent advances in the synthesis and functions of reconfigurable interlocked DNA nanostructures. J Am Chem Soc. 2016;138:5172-85. Epub Mar. 28, 2016.
Maruyama et al., Characterization of interpolyelectrolyte complexes between double-stranded DNA and polylysine comb-type copolymers having hydrophilic side chains. Bioconjugate Chem. 1998;9:292-9. Epub Feb. 24, 1998.
Shih et al., poster. DNA-Based Molecular Containers and NMR Alignment Media. 2006. 1 page.
Steinhauer et al., DNA origami as a nanoscopic ruler for super-resolution microscopy. Angew Chem Int Ed Engl. 2009;48(47):8870-3. doi: 10.1002/anie.200903308.
Walsh et al., DNA cage delivery to mammalian cells. ACS Nano. 2011;5(7):5427-32. Epub Jun. 22, 2011.
Weizmann et al., A polycatenated DNA scaffold for the one-step assembly of hierarchical nanostructures. Proc Nat Acad Sci. Apr. 8, 2008;105(14):5289-94.
Yan et al., DNA-templated self-assembly of protein arrays and highly conductive nanowires. Science. Sep. 26, 2003;301(5641):1882-4.
Yang et al., Nanostructures as programmable biomolecular scaffolds. Bioconjug Chem. Aug. 19, 2015;26(8):1381-95. doi:10.1021/acs.bioconjchem.5b00194. Epub May 11, 2015.
Zhang et al., Structural DNA nanotechnology: state of the art and future perspective. J Am Chem Soc. Aug. 13, 2014;136(32):11198-211.doi:10.1021/ja505101a. Epub Jul. 16, 2014.
Zhang et al., Dynamic DNA nanotechnology using strand-displacement reactions. Nat Chem. Feb. 2011;3(2):103-13. doi: 10.1038/nchem.957.

(56) References Cited

OTHER PUBLICATIONS

Zhu et al. Hollow mesoporous silica poly-(l-lysine) particles for codelivery of drug and gene with enzyme-triggered release property. J Phys Chem C. 2011;115:13630-5. Epub Jun. 15, 2011.

Douglas et al., Rapid prototyping of 3D DNA-origami shapes with caDNAno. Nucleic Acids Res. Aug. 2009;37(15):5001-6. doi: 10.1093/nar/gkp436. Epub Jun. 16, 2009.

Valero et al., Interlocked DNA topologies for nanotechnology. Curr Opin Biotechnol. May 12, 2017;48:159-67.

Extended European Search Report dated Feb. 11, 2022 for Application No. EP 21187413.6.

\* cited by examiner

NUCLEIC ACID NANOSWITCH CATENANES

RELATED APPLICATIONS

This application is a national stage filing under 35 U.S.C. § 371 of international application No. PCT/US2017/021562, filed Mar. 9, 2017, which claims the benefit under 35 U.S.C. § 119(e) of U.S. provisional application No. 62/306,764, filed Mar. 11, 2016, each of which is incorporated by reference herein its entirety.

BACKGROUND

Single-molecule sandwich-ELISA typically works by recruiting an amplifiable reporter to the surface of a bead or a plate well. This typically results in significant false positives due to residual nonspecific binding of the reporter to the surface. For example, if a washing procedure eliminates 99.9999% of one billion non-specific reporters, then 1000 false-positive reporters still remain. In the specific case of sandwich-ELISA assays, false positives due to nonspecific binding reduce the effective sensitivity of sandwich-ELISA assay to ~10,000 target molecules.

SUMMARY

Provided herein, in some aspects, are compositions and methods that that enable zeptomolar (zM) limit-of-detection, automated, high-throughput, low-cost quantitation of analytes from blood or other sources. The nucleic acid-based "nanoswitch catenanes" of the present disclosure function as immunoassays to aid in the detection of biomolecules of interest, for example. Relative to existing immunoassays, the compositions and methods as provided herein enable high sensitivity/low background biomolecule detection, reduced potential for contamination, increased accuracy for small sample volumes, increased speed and throughput, and lower cost.

Some aspects of the present disclosure provide a nanoswitch catenane comprising (a) a polymer (e.g., a single-stranded or double-stranded nucleic acid) comprising (i) a first terminal domain comprising a first functional group (e.g., an azide or alkyne), a first binding partner (e.g., an antibody, aptamer or nanobody), and a second functional group (e.g., a thiol or nucleic acid), (ii) a second terminal domain comprising a third functional group (e.g., a thiol or nucleic acid), a second binding partner (e.g., an antibody, aptamer or nanobody), and a fourth functional group (e.g., an azide or alkyne), wherein the first and second terminal domains are linked to form a host ring, wherein the first and fourth functional groups react in the presence of a reaction agent to form a link (e.g., a covalent link), wherein the first and fourth binding partners bind specifically to a biomolecule of interest to form a link (e.g., non-covalent link), and wherein the second and third functional groups form a link (e.g., a covalent link) that breaks in the presence of a dissociation agent, and (b) a (e.g., at least one or at least two) circular nucleic acid guest ring catenated with the host ring.

A nanoswitch catenane, in some aspects, comprises (a) a polymer (e.g., a single-stranded or double-stranded nucleic acid) comprising a first and second terminal domain linked to each other to form a host ring by one of a first, second or third switchable bridges (links between functional groups that form or break in the presence of a particular agent), wherein the first switchable bridge is formed in the presence of a reaction agent through the reaction of two cognate functional groups (functional groups that can react with each other, e.g., to form a covalent or noncovalent bond), each linked to a terminal domain of the polymer, wherein the second switchable bridge is formed in the presence of a biomolecule of interest through specific binding of the biomolecule of interest to two cognate binding partners (e.g., antibodies), each linked to a terminal domain of the polymer, and wherein the third switchable bridge is a link (e.g., a covalent link) between two cognate functional groups that breaks in the presence of a dissociation agent, and (b) a circular nucleic acid guest ring catenated with the host ring.

In some embodiments, a nanoswitch catenane comprises (a) a single-stranded nucleic acid comprising (i) a first terminal domain comprising an azide, an antibody, and a thiol group, and (ii) a second terminal domain comprising an alkyne, an antibody, and a thiol group, wherein antibody of (i) and the antibody of (ii) bind specifically to a biomolecule of interest, and (b) a circular nucleic acid guest ring catenated with the host ring.

In other embodiments, a nanoswitch catenane comprises only two switchable bridges. For example, a nanoswitch catenane may comprise a polymer (e.g., a single-stranded or double-stranded nucleic acid) comprising (i) a first terminal domain comprising a first functional group and a first binding partner (e.g., an antibody, aptamer or nanobody), (ii) a second terminal domain comprising a second functional group and a second binding partner (e.g., an antibody, aptamer or nanobody), wherein the first and second terminal domains are linked to form a host ring, wherein the first and second functional groups form a link that breaks in the presence of a dissociation agent and react in the presence of a reaction agent to form a link, wherein the first and fourth binding partners bind specifically to a biomolecule of interest to form a link (e.g., non-covalent link), and (b) a (e.g., at least one or at least two) circular nucleic acid guest ring catenated with the host ring.

Aspects of the present disclosure also provide methods of detecting a biomolecule of interest, comprising in the following ordered steps: (a) incubating a sample suspected of containing a biomolecule of interest with a nanoswitch catenane as described herein to permit specific binding of a biomolecule of interest to the first and second binding partners, thereby forming a reaction mixture; (b) incubating a dissociation reagent with the reaction mixture to break the link (e.g., covalent link) between the second and third functional groups of the nanoswitch catenane and to permit release of the guest ring from the host ring; and (c) incubating the reaction mixture with a reaction agent to form a link (e.g., covalent link) between the first and fourth functional groups of the nanoswitch catenane. The method may also include assaying the nanoswitch catenane for the presence or absence of the guest ring.

DESCRIPTION

Nanoswitch catenanes of the present disclosure may be used to detect a particular molecule of interest. They typically include a polymer (e.g., nucleic acid) comprising (i) a first terminal domain (one end of the polymer) comprising a first functional group, a first binding partner, and a second functional group, and (ii) a second terminal domain (the other end of the polymer) comprising a third functional group, a second binding partner, and a fourth functional group. The first and second terminal domains are linked to form a host ring, the first and fourth functional groups react in the presence of a reaction agent to form a link, the first and second binding partners bind specifically to a biomolecule of interest to form a link, and the second and third functional groups form a link that breaks in the presence of a dissociation agent. The nanoswitch catenanes also typically include at least two circular nucleic acid guest ring catenated with the host ring. When the nanoswitch catenanes are used for target biomolecule detection, the guest rings function as indicators of the presence or absence of the target biomolecule in a sample, for example, as discussed below.

Figure 1A:
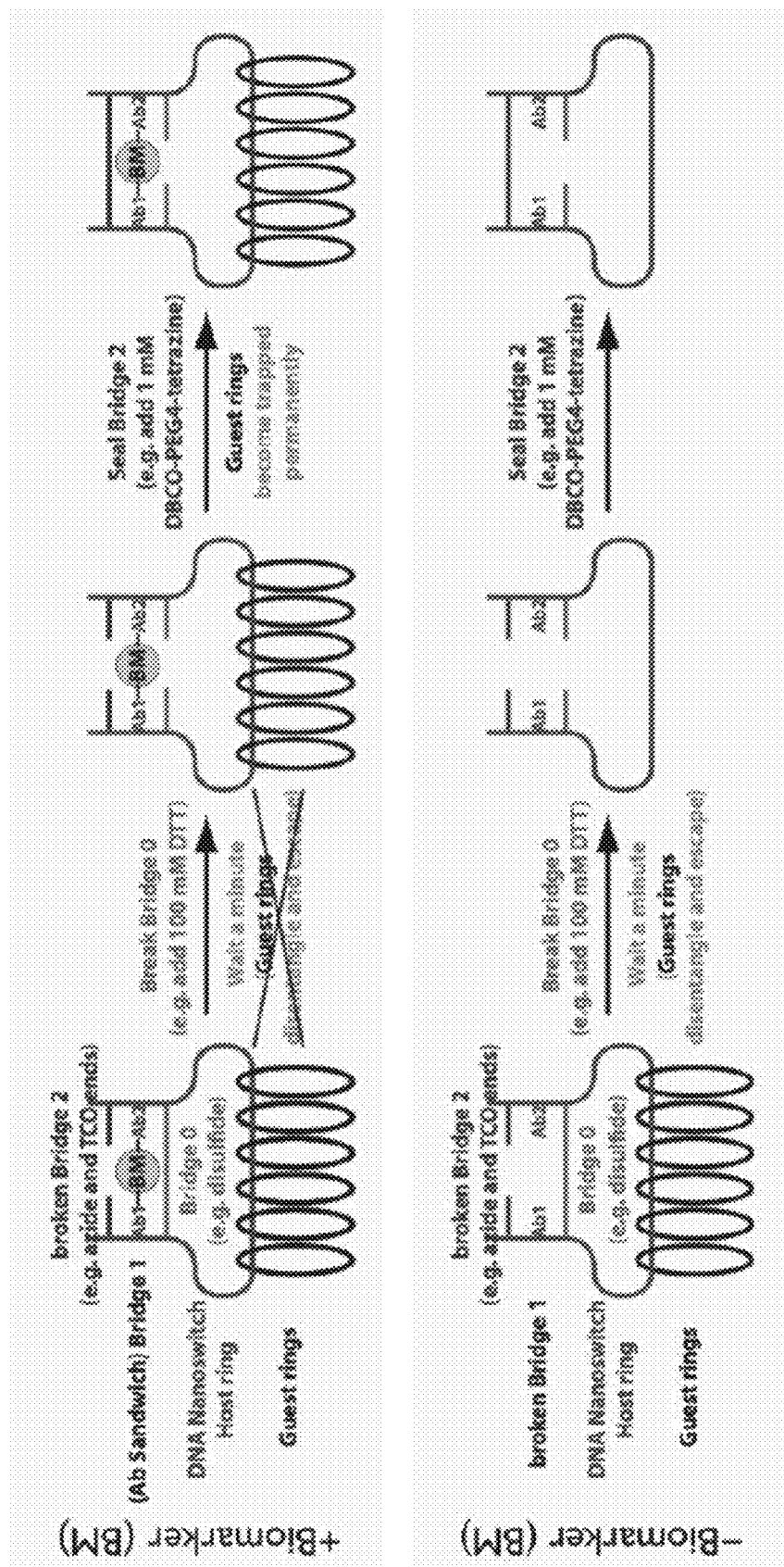
FIGS. 1A and 1B show examples of a DNA nanoswitch catenane. Binding of the biomarker protects the catenane from disentanglement in between breaking of bridge 0 and sealing of bridge 2. DNA nanoswitch catenanes may offer 100× greater sensitivity (down to 10 aM) for gel analysis. Catenanes can be very large (e.g., more dye, higher signal); a large change in size upon catenane disassembly results in lower background.
Figure 1B:
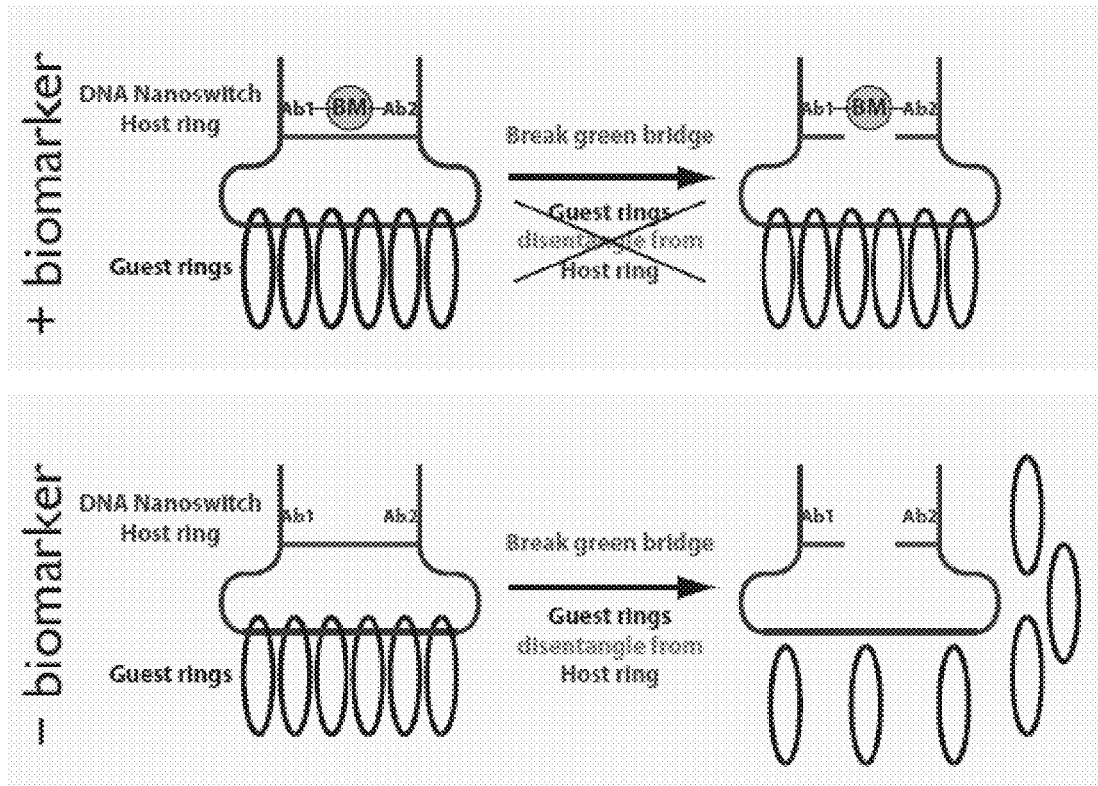

FIG. 1 provides an example of a nanoswitch catenane. The host (master) ring may be a DNA loop closed by one of three switchable bridges. In this example shown in FIG. 1, bridge 0 (e.g., a disulfide bond) starts closed and is opened rapidly upon addition of a chemical trigger (e.g., addition of 100 mM DTT). Bridge 2 (e.g., between azide and an alkyne) starts open and is closed (forms a link) upon addition of another chemical trigger (e.g., DBCO-PEG4-tetrazine, to activate a click chemistry reaction). Bridge 1 is formed in the presence of a target biomolecule that is bound specifically by the antibodies (Ab 1 and Ab2), for example, that are linked to the host ring. The guest rings (e.g., nucleic acids encoding components required for an amplification reaction) are released from the host ring, unless bridge 1 remains closed for the full duration between the two triggered events (opening of bridge 0 and closing of bridge 2). If bridge 1 remains closed (in the presence of a target biomolecule bound to the antibodies), then the guest rings remain concatenated with the host ring, in close proximity to one another, and can participate in a read-out amplification reaction, indicative of the presence of the target biomolecule.

Release of the guest rings should be faster than re-closure of bridge 0, so that the guest rings have time to fall off the host ring, to avoid false positives. This may be achieved, for example, by using mechanical strain (e.g., mechanical equilibrium as a rigid, straight rod) such that it takes longer to bend the opened catenane back into a cyclic configuration.

Digital counting via nanoswitch catenanes, then, relies on decomposition of each of a large number (e.g., six billion in a volume of 1 μL or 10 nM) of reporters that fail to complete an antibody-sandwich (bridge 1) loop for a specified time interval (e.g., one minute incubation between sequential mixing steps that open bridge 0 and close bridge 2, respectively). Decomposition can be driven arbitrarily close to completion, thus false positives can be reduced effectively to zero. It is possible to multiplex biomarker detection, and therefore it is possible to do ratiometric counting, thereby eliminating calibration artifacts that often plague biodetection efforts.

Figure 2:
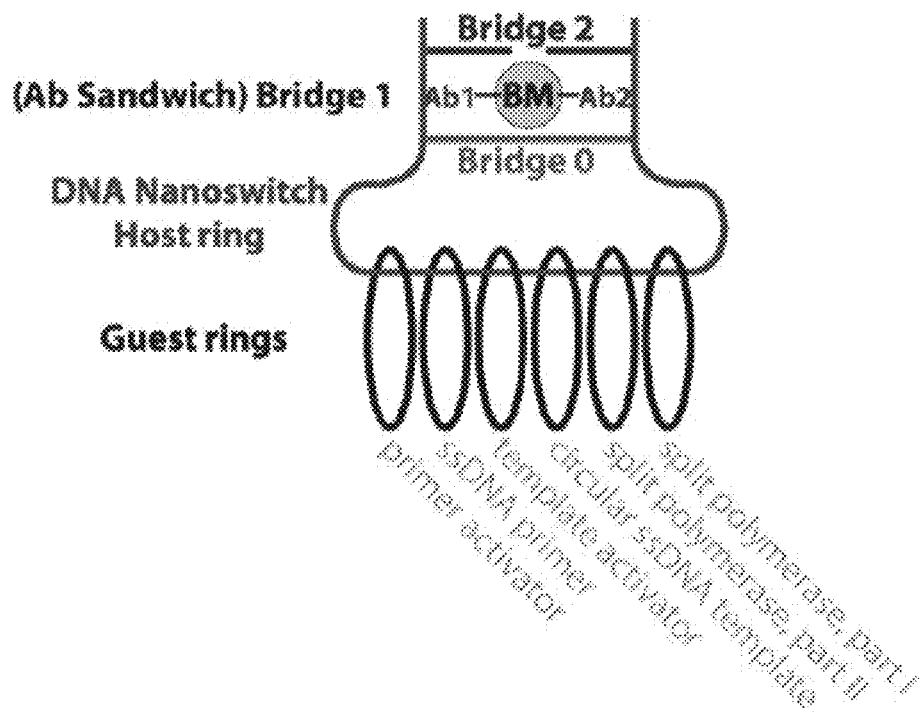
FIG. 2 shows an example of a rolling-circle-amplification (RCA) reporter output for surviving DNA nanoswitch catenanes. Disentanglement of the nanoswitch catenane causes the various components to become highly dilute, creating an insurmountable entropic barrier to even transient reconstitution of a competent RCA assembly. If the components remain together on the catenane, then RCA can be initiated by addition of dNTPs, and a sizeable sequence-barcodeable record of detection can thus be generated.

FIG. 2 provides an example of a sequence-barcodeable reporter that can be implemented using a nanoswitch catenane. In this example, survival of the reporter (guest rings) is followed by addition of dNTPs and subsequent polymerization to create a large record of the detection event (~100 kb). Because the sequence is determined by the template encoded by a guest ring, it can be barcoded in a sequence-dependent fashion. This system in this example functions well if the various components of a competent rolling circle amplification (RCA) assembly can be destroyed (e.g., irreversibly and completely destroyed) upon disentanglement of the guest rings (e.g., circular nucleic acids) from the host ring. This can be accomplished, for example, by requiring a large number of weakly interacting components be present before polymerization can initiate. In this example, the RCA assembly is designed to have six necessary components, held together at millimolar concentration in the catenane. The polymerase is split into two pieces. The template is designed to have its primer binding site sequestered in an intramolecular hairpin that can be opened by strand displacement by the single-stranded template activator. The primer is designed to be sequestered in an intramolecular hairpin that can be opened by strand displacement by the single-stranded primer activator. If the host ring opens and the guest rings are released, then their concentrations will be diluted to the nanomolar range. Each component will become diluted by a factor of a million. To spontaneously return all six components to the millimolar effective concentration (e.g., by adjusting the affinities of the components to each other to get an initiation rate of one per second) for initiation of polymerization uses payment of a large entropic cost equivalent to $(kT \ln 1e6)^5$. The fraction of time that this will happen spontaneously will be $(1e-6)^5=1e-30$. Thus, for a population of 1e10 reporters over the course of a day, this essentially should never happen.

In some embodiments, nanoswitch catenanes are used to detect an early infection (e.g., bacterial or viral). For example, 17 denatured HIV virions in 5 L blood*3000 p24 copies per HIV virion 51,000 p24 copies in 5 L=~ten p24 copies in 1 mL blood draw.

In some embodiments, nanoswitch catenanes are used to detect micro tumors. For example, 10 cell micro-tumor secretes 50,000 proteins in 5 L blood=~ten protein-marker copies in 1 mL blood draw.

In some embodiments, nanoswitch catenanes are used to detect rare alleles. For example, 1 part mutant gene copy to 1e12 parts wildtype gene copies without requirement for deep sequencing.

In some embodiments, nanoswitch catenanes are used to detect biomolecules in saliva samples, urine samples, or blood samples (e.g., from a single drop of blood).

The host ring of the nanoswitch catenanes may be formed from any polymer that is capable of forming a ring and to which functional groups can be attached. An example of a polymer is a nucleic acid (a polymer of nucleotide monomers). Thus, a polymer host ring may be a single-stranded, double-stranded, or partially double-stranded (having single-stranded and double-stranded regions) deoxyribonucleic acid (DNA) or ribonucleic acid (RNA). In some embodiments, the nucleic acid is a DNA, such as a single-stranded DNA.

The length of the polymer (e.g., single-stranded nucleic acid) may vary. In some embodiments, the polymer host ring has a length of 20 nm to 3,000 nm. For example, the polymer may have a length of 20-100, 20-200, 20-300, 20-400, 20-500, 20-600, 20-700, 20-800, 20-900, 20-1000, 20-2000, or 20-3000 nm. In some embodiments, the polymer has a length of 20, 30, 40, 50, 60, 70, 80, 90, 100, 150, 200, 250, 300, 350, 400, 450, 500, 550, 600, 650, 700, 750, 800, 850, 900, 950, 1000, 1500, 2000, 2500, or 3000 nm. The length of the polymer host ring may be shorter than 20 nm or longer than 3,000 nm.

In some embodiments, the polymer is a single-stranded nucleic acid that has a length of 100 nucleotides to 10,000 nucleotides. For example, the single-stranded nucleic acid may have a length of 100-200, 100-300, 100-400, 100-500, 100-1000, 100-2000, 100-5000 or 100-10,000. In some embodiments, the single-stranded nucleic acid has a length of 100, 150, 200, 250, 300, 350, 400, 450, 500, 550, 600, 650, 700, 750, 800, 850, 900, 950 or 10000 nucleotides. The length of the single-stranded nucleic acid may be shorter than 100 nucleotides or longer than 10,000 nucleotides.

A "terminal domain" is a region (contiguous stretch of nucleotides) of the polymer (e.g., single-stranded nucleic acid located) located at an end (e.g., the 3' end or the 5' end) of the polymer (e.g., nucleic acid). The length of a terminal domain may vary. In some embodiments, the terminal domain has a length of 3 nm to 100 nm. For example, the terminal domain may have a length of 3-10, 3-20, 3-30, 3-40, 3-50, 3-60, 3-70, 3-80, 3-90 or 3-100 nm. In some embodiments, the terminal domain has a length of 3, 4, 5, 6, 7, 8, 9, 10, 20, 30, 40, 50, 60, 70, 80, 90 or 100 nm.

In embodiments wherein the polymer is a nucleic acid, the terminal domain may have a length of 10 nm to 300 nucleotides. For example, the terminal domain may have a length of 10-20, 10-30, 10-40, 10-50, 10-60, 10-70, 10-80, 10-90, 10-100, 10-200 or 10-300 nucleotides. In some embodiments, the terminal domain has a length of 10, 20, 30, 40, 50, 60, 70, 80, 90, 100, 200 or 300 nucleotides.

The distance between any two functional groups along a terminal domain of a host ring may also vary. For example, the distance between the first functional group and the first biomolecule binding partner (e.g., antibody) may be 3-10 (e.g., 3, 4, 5, 6, 7, 8, 9 or 10) nm. Likewise, the distance between the first biomolecule binding partner (e.g., antibody) and the second functional group may be 3-10 (e.g., 3, 4, 5, 6, 7, 8, 9 or 10) nm.

In embodiments wherein the polymer is a nucleic acid, the distance between the first functional group and the first biomolecule binding partner (e.g., antibody) may be 10-30 (e.g., 10, 15, 20, 25, or 30) nucleotides. Likewise, the distance between the first biomolecule binding partner (e.g., antibody) and the second functional group may be 10-30 nucleotides (e.g., 10, 15, 20, 25, or 30).

The terminal domains of a polymer (e.g., single-stranded nucleic acid) may be linked to each other to form a circular nucleic acid, referred to as a "host ring," through one of three switchable bridges. A "switchable bridge" is a link between functional groups that forms or breaks in the presence of a particular agent (e.g., reaction agent or dissociation agent). Examples of switchable bridges include bonds formed via a "click chemistry" reaction (e.g., a between an azide and an alkyne), protein-protein binding (e.g., one or more antibodies binding to a target protein/antigen), a disulfide bond (between two thiols).

A "first biomolecule binding partner" and a "second biomolecule binding partner" are any molecules that bind to the same target biomolecule to form another one of the three switchable bridges linking the terminal domains to each other (via a non-covalent link). In some embodiments, the first and second biomolecule binding partners are proteins or peptides. For example, the first and second biomolecule binding partners may be antibodies that bind to different epitopes of the same antigen. Thus, in some embodiments, the first and second biomolecule binding partners are antibodies (e.g., monoclonal, polyclonal, human, humanized or chimeric). In some embodiments, the first and second biomolecule binding partners are antibody fragments (e.g., Fab, F(ab')2, Fc, scFv, or vhh). The biomolecule binding partners may also be nanobodies or aptamers. Other protein-protein binding partners may be used.

A "first functional group" and a "fourth functional group" are functional groups that react with each other to form a link (bond, such as a covalent bond or a non-covalent bond), which forms one of the three switchable bridges linking the terminal domains to each other. In some embodiments, this bridge is formed through a click chemistry (azide-alkyne cycloaddition) reaction (e.g., V. V. Rostovtsev, et al., *Angew. Chem. Int. Ed.*, 2002, 41, 2596-2599; and F. Himo, et al. *J. Am. Chem. Soc.*, 2005, 127, 210-216, each of which is incorporated herein by reference). Thus, in some embodiments, one of the first or fourth functional group is an azide, while the other of the first or fourth functional groups is an alkyne. For example, the first functional group may be azide, and the fourth functional group may be trans-cyclooctene (TCO). Other click chemistry functional groups may be used.

A "second functional group" and a "third functional group" are functional groups that react with each other to form a link (bond, such as a covalent bond or a non-covalent bond), which forms yet another of the three switchable bridges linking the terminal domains to each other. This bridge breaks (dissociates) in the presence of a dissociation agent. A "dissociation agent" is an agent (e.g., chemical) that breaks the bond (e.g., covalent bond) between the second and third functional groups. In some embodiments, the second and third functional groups are thiol groups that react with each other to form a disulfide bridge. Thus, in some embodiments, the dissociation agent is dithiothreitol (DTT). In some embodiments, the concentration of DTT is 50 mM-200 mM. For example, the concentration of DTT may be 100 mM. Other functional groups may be used.

Figure 3A:
FIGS. 3A-3B show an example of a nucleic acid-based switchable bridge in the closed configuration (FIG. 3A) and in the open configuration (FIG. 3B).
Figure 3B:
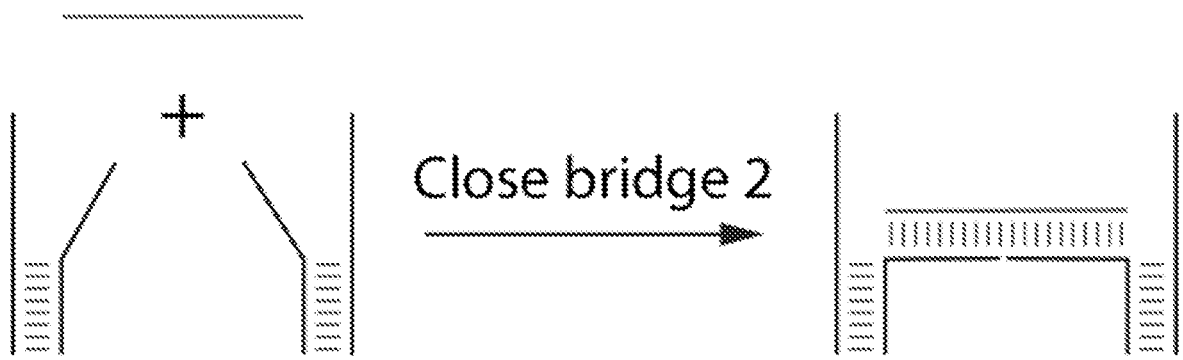

In some embodiments, the functional groups are single-stranded nucleic acids. For example, as shown in FIG. 3A, a switchable bridge may be formed by binding of a first and second nucleic acid (each respectively linked to the first and second terminal domain of the host ring) to a third nucleic acid that comprises a toehold domain (see, e.g., WO 2012/058488, published 3 May 2012, incorporated herein by reference). Hybridization of the two nucleic acid functional groups to a third nucleic acid (that is longer than the length of the two nucleic acid functional groups combined) forms a switchable bridge that can be dissociated through a strand displacement reaction (see, e.g., Zhang, D. Y. et al. *Nature Chemistry* 3, 103-113, 2011) in the presence of a fourth nucleic acid. The third nucleic acid (e.g., single stranded nucleic acid) comprise at least three domains, one of which is complementary to and binds to the first nucleic acid functional group, one of which is complementary to and binds to the second nucleic acid functional group, and yet another of which remains single-stranded (forms a toehold domain). The fourth nucleic acid is complementary to and binds to the three domains of the third nucleic acid. When bound to the third nucleic acid, this fourth nucleic acid displaces the first and second nucleic acid functional groups, thereby opening the switchable bridge. The switchable bridge may later be closed by the additional of a fifth nucleic acid that is complementary to and binds to both the first and second nucleic acid functional groups (FIG. 3B).

The length of each nucleic acid functional group, or the third and fourth nucleic acids, may vary. In some embodiments, the length of a nucleic acid functional group is 10-100 nucleotides. For example, a nucleic acid functional group may have a length of 10-20, 10-30, 10-40, 10-50, 10-60, 10-70, 10-80, 10-90, 20-30, 20-40, 20-50, 20-60, 20-70, 20-80, 20-90 or 20-100 nucleotides. In some embodiments, a nucleic acid functional group may have a length of 10, 20, 30, 40, 50, 60, 70, 80, 90 or 100 nucleotides. The length and composition of the third nucleic acid (comprising the toehold domain) and the fourth nucleic acid (complementary to the length of the third nucleic acid) depends on the length and composition of the nucleic acid functional group(s).

In some embodiments, a nanoswitch catenane comprises only two switchable bridges: one formed by nucleic acid functional groups that are modulated by a toehold-mediated strand displacement reaction (see, e.g., FIG. 3A-3B) and one formed by specific binding of a target biomolecule to two binding partners located on the host ring.

The nanoswitch catenane comprises "guest rings," which are circular nucleic acids (e.g., double-stranded or single-stranded) concatenated with the host ring. The guest rings are released from the host ring only in the absence of a target biomolecule, following two triggered events—opening of one bridge (e.g., disulfide bridge) and closing of another bridge (e.g., click chemistry bridge). The host ring, in some embodiments, comprises at least 2 guest rings. For example, a host ring may comprise at least 2, 3, 4, 5, 6, 7, 8, 9 or 10 rings. In some embodiments, a host ring comprises 2-10 or 2-20 guest rings.

Thus, release of the guest rings from the host ring indicates the absence of a target biomolecule in a sample, for example.

Methods of catenating molecules, such as nucleic acid molecules, are known (see, e.g., Ashton, P. R. et al. *Journal of the Chemical Society, Chemical Communications* (9): 634, 1991; Cesario, M. et al. *Journal of the Chemical Society, Chemical Communications* (5): 244, 1985; Li, Q. et al. *Chembiochem*. 17(12):1127-31, 2016; Zhang, L. M. et al. *Nat Commun*. 7:12074, 2016; Lu, C. H. et al. *J Am Chem Soc*. 138(16):5172-85, 2016; Lu, C. H. et al. *Nano Lett*. 15(10):7133-7, 2015; *Nat Commun*. 5:4279, 2014; and Gaillard, C. et al. *PLoS One*. 10(3):e0119368, 2015, each of which is incorporated herein by reference). Generally, a catenane is a mechanically-interlocked molecular architecture that includes two or more interlocked macrocycles.

The guest rings, when captured on the host ring, may encode components of a particular reaction, such as a rolling circle amplification reaction. For example, one circle may encode a template (e.g., circular single-stranded DNA (ssDNA) template) with primer binding sites, another circle may encode a template activator, another circle may encode a ssDNA primer, another circle may encode a primer activator, and another circle may encode a polymerase or part of a polymerase (while yet another circle encodes the other part of the polymerase). If the guest rings remain together on the nanoswitch, then rolling circle amplification can be initiated by addition of dNTPs, and a sizeable sequence-barcodeable record of detection can be generated.

As another example, the guest rings may encode components required for a hybridization chain reaction (see, e.g., Evanko, D. Nature Methods—1, 186-187 (2004); and Choi, H. M. T. *ACS Nano*, 2014, 8(5), pp 4284-4294 (2014), incorporated herein by reference).

Nanoswitch catenanes, in some embodiments, comprise (a) a single-stranded nucleic acid comprising a first and second terminal domain linked to each other to form a host ring by one of a first, second or third switchable bridges, wherein the first switchable bridge is formed in the presence of a reaction agent through the reaction of two cognate functional groups, each linked to a terminal domain of the single-stranded nucleic acid, wherein the second switchable bridge is formed in the presence of a biomolecule of interest through binding of the biomolecule of interest to two cognate antibodies (antibodies that specifically bind to the biomolecule), each linked to a terminal domain of the single stranded nucleic acid, and wherein the third switchable bridge is a covalent link between two cognate functional groups that breaks in the presence of a dissociation agent, and (b) a circular nucleic acid guest ring catenated with the host ring.

Nanoswitch catenanes, in other embodiments, comprise (a) a single-stranded nucleic acid comprising (i) a first terminal domain comprising an azide, an antibody, and a thiol group, and (ii) a second terminal domain comprising an alkyne, an antibody, and a thiol group, wherein antibody of (i) and the antibody of (ii) bind specifically o a biomolecule of interest, and (b) a circular nucleic acid guest ring catenated with the host ring.

In some embodiments, the azide and the alkyne are conjugated to form a covalent link.

In some embodiments, the antibodies are bound to a biomolecule of interest to form a non-covalent link.

In some embodiments, the thiol groups are conjugated to each other to form a covalent link.

Also provided herein are methods of detecting a biomolecule of interest, comprising in the following ordered steps: (a) incubating a sample suspected of containing a biomolecule of interest with a nanoswitch catenane to permit binding of a biomolecule of interest to the first and second binding partners, thereby forming a reaction mixture; (b) incubating a dissociation reagent with the reaction mixture to break the covalent link between the second and fourth functional groups of the nanoswitch catenane and to permit release of the guest ring from the host ring; (c) incubating the reaction mixture with a reaction agent to form a covalent link between the first and third functional groups of the nanoswitch catenane; and (d) assaying the nanoswitch catenane for the presence or absence of the guest ring.

A "dissociation agent" is an agent or mixture of agents that cause the bond (e.g., covalent bond) between two functional groups to break. Dithiothreitol (DTT) is an example of a dissociation agent that may be used to break the disulfide bond between thiol groups.

A "reaction agent" is an agent or mixture of agents that cause the formation of a bind (e.g., a covalent bond) between two functional groups. DBCO-PEG4-tetrazine is an example of a reaction agent that may be used to form a bond between an azide and an alkyne.

A "biomolecule of interest" may be a protein or a nucleic acid, for example. In some embodiments, a biomolecule of interest is a virus, virion or viral particle. In some embodiments, the biomolecule is an antigen, such as a tumor antigen (e.g., micro tumor antigen). In some embodiments, the biomolecule of interest is an allele (e.g., a rare allele).

Additional Embodiments

Additional embodiments are described in the following numbered paragraphs:

1. A nanoswitch catenane comprising:
   (a) a single-stranded nucleic acid comprising
   (i) a first terminal domain comprising a first functional group, a first binding partner, and a second functional group;
   (ii) a second terminal domain comprising a third functional group, a second binding partner, and a fourth functional group,
   wherein the first and second terminal domains are linked to form a host ring, wherein the first and fourth functional groups react in the presence of a reaction agent to form a link, wherein the first and second binding partners specifically bind to a biomolecule of interest to form a link, and wherein the second and third functional groups form a link that breaks in the presence of a dissociation agent; and
   (b) at least two circular nucleic acid guest rings catenated with the host ring.
2. The nanoswitch catenane of paragraph 1, wherein the nucleic acid is a single-stranded nucleic acid.
3. The nanoswitch catenane of paragraph 1 or 2, wherein the first binding partner is located between the first functional group and the second functional group, and wherein the second binding partner is located between the third functional group and the fourth functional group, and wherein the first and fourth functional groups are located at the distal end of the terminal domain.
4. The nanoswitch catenane of any one of paragraphs 1-3, wherein the link formed between the first and fourth functional groups is a covalent link.
5. The nanoswitch catenane of any one of paragraphs 1-4, wherein the link formed between the second and third functional groups is a covalent link.
6. The nanoswitch catenane of any one of paragraphs 1-5, wherein the link formed between the first and second binding partners is a non-covalent link.
7. The nanoswitch catenane of any one of paragraphs 1-6, wherein the single-stranded nucleic acid is a single-stranded deoxyribonucleic acid (DNA).
8. The nanoswitch catenane of any one of paragraphs 1-7, wherein the single-stranded nucleic acid has a length of 100 nucleotides to 1000 nucleotides.
9. The nanoswitch catenane of any one of paragraphs 1-8, wherein the first and/or second terminal domain has a length of 30 nucleotides to 100 nucleotides.
10. The nanoswitch catenane of any one of paragraphs 1-9, wherein one of the first or third functional groups is an azide, and wherein the other of the first or third functional groups is an alkyne.
11. The nanoswitch catenane of any one of paragraphs 1-10, wherein the first functional group is azide, and the second functional group is trans-cyclooctene (TCO).
12. The nanoswitch catenane of any one of paragraphs 1-11, wherein the first and second biomolecule binding partners are proteins.
13. The nanoswitch catenane of paragraph 12, wherein the proteins are antibodies, aptamers, or nanobodies.
14. The nanoswitch catenane of any one of paragraphs 1-13, wherein the second and fourth functional groups are thiol groups.
15. The nanoswitch catenane of any one of paragraphs 1-14, wherein the catenane comprises at least 3 guest rings.
16. The nanoswitch catenane of paragraph 15, wherein the catenane comprises 3-20 guest rings.
17. The nanoswitch catenane of any one of paragraphs 1-16, wherein the guest ring is linked to or encodes a component of an amplification reaction.
18. The nanoswitch catenane of paragraph 17, wherein the amplification reaction is a rolling-circle amplification reaction or a hybridization chain reaction.
19. A nanoswitch catenane comprising:
   (a) a single-stranded nucleic acid comprising a first and second terminal domain linked to each other to form a host ring by one of a first, second or third switchable bridges,
   wherein the first switchable bridge is formed in the presence of a reaction agent through the reaction of two cognate functional groups, each linked to a terminal domain of the single-stranded nucleic acid,
   wherein the second switchable bridge is formed in the presence of a biomolecule of interest through binding of the biomolecule of interest to two cognate antibodies, each linked to a terminal domain of the single stranded nucleic acid, and
   wherein the third switchable bridge is a link between two cognate functional groups that breaks in the presence of a dissociation agent; and
   (b) a circular nucleic acid guest ring catenated with the host ring.
20. A nanoswitch catenane comprising:
   (a) a single-stranded nucleic acid comprising
   (i) a first terminal domain comprising an azide, an antibody, and a thiol group, and
   (ii) a second terminal domain comprising an alkyne, an antibody, and a thiol group, wherein antibody of (i) and the antibody of (ii) specifically bind to a biomolecule of interest; and
   (b) a circular nucleic acid guest ring catenated with the host ring.
21. The nanoswitch catenane of paragraph 20, wherein the azide and the alkyne are conjugated to form a covalent link.
22. The nanoswitch catenane of paragraph 20 or 21, wherein the antibody of (i) and the antibody of (ii) are bound to a biomolecule of interest to form a non-covalent link.
23. The nanoswitch catenane of any one of paragraphs 20-22, wherein the thiol groups are conjugated to form a covalent link.
24. A method of detecting a biomolecule of interest, comprising in the following ordered steps:
   (a) incubating a sample suspected of containing a biomolecule of interest with a nanoswitch catenane of any one of paragraphs 1-18 to permit binding of a biomolecule of interest to the first and second binding partners, thereby forming a reaction mixture;
   (b) incubating a dissociation reagent with the reaction mixture to break the link between the second and fourth functional groups of the nanoswitch catenane and to permit release of the guest ring from the host ring;
   (c) incubating the reaction mixture with a reaction agent to form a link between the first and third functional groups of the nanoswitch catenane; and
   (d) assaying the nanoswitch catenane for the presence or absence of the guest ring.
25. A nucleic acid nanoswitch catenane comprising
   (a) a single-stranded nucleic acid comprising a 5' terminal domain joined to a 3' terminal domain through one of three bridges, wherein the 5' terminal domain comprises a first antibody and the 3' terminal domain comprises a second antibody,
   wherein the first bridge and the second bridge are formed by chemical bonds, and wherein the third bridge is formed by binding of the first antibody and the second antibody to a target biomolecule, thereby forming a nucleic acid ring; and (b) a plurality of circular nucleic acids catenated with the nucleic acid ring.

26. The nucleic acid nanoswitch catenane of paragraph 25, wherein the first bridge is formed by a disulfide bond.
27. The nucleic acid nanoswitch catenane of paragraph 25 or 26, wherein the second bridge is formed by chemical crosslinking.
28. The nucleic acid nanoswitch catenane of any one of paragraph 25-27, wherein the plurality comprises at least 3, at least 4, at least 5, or at least 6 circular nucleic acids.
29. The nucleic acid nanoswitch catenane of paragraph 28 wherein the plurality comprises 6 circular nucleic acid.
30. The nucleic acid nanoswitch catenane of paragraph 29, wherein each of the circular nucleic acids is linked to or encodes one component of a rolling circle amplification reaction.

EXAMPLES

Example 1

A rolling circle amplification system is produced, which requires convergence of a large number of weakly interacting components. When sequestered on a nanoswitch catenane, the effective concentrations of the components will be high enough to initiate polymerization. Kinetic proofreading can ensure disentangling of every nanoswitch catenane not bound by target; the released components will be too dilute for simultaneous reconstitution (zero background). Sequence-barcoded rolling-circle amplicons can be discriminated via fluorescence hybridization readout (multiplexed).

Example 2

For the ultimate in antibody-based detection, one seeks low false negatives and low false positives, where it is especially critical to drive false positives very close to zero (1e-20 or lower), but not so critical to drive false negatives below 10% or so. In general, it is not difficult to keep false negatives below 10% if a method can be obtained for driving false positives very close to zero. There are two stages:

In the first stage, a large excess of reporters are deployed for efficient capture of the target molecules, followed by removal or destruction of any target-free reporters. Here low false negatives means that most target molecules are captured by a reporter, and that most of these target-bound reporters survive the removal/destruction step. Low false positives means that virtually every single analyte-free reporter is destroyed or removed. Nanoswitch catenanes drive false positives to zero in the first stage by using kinetic proofreading (see below).

In the second stage, the surviving reporters are amplified to create a countable signal. Here low false negatives means that most reporters are successfully amplified. Low false positives means that spontaneous amplification in the absence of reporters is completely or almost completely eliminated. Nanoswitch catenanes drive false positives to zero in the second stage by holding together several required, weakly interacting components of a reporter when the catenane is preserved, but reliably release and therefore dilute these components into bulk solution whenever the integrity of a catenane is breached, even transiently. The high entropy cost to bringing these components back together from bulk solution effectively suppresses spontaneous reporter reconstitution to zero.

This example describes a solution-based, kinetic-proof-reading immunoassay to overcome these limitations. An example immunoassay is described, as follows, in the context of a specific test: detection of a protein analyte at 1 zM in blood, or a mere six copies in 10 mL, against a background of 6e18 non-target proteins (assuming 1 mM plasma protein concentration).

(1) Two opposing goals are low false negatives versus low false positives. To achieve low false negatives in the first stage, one needs to deploy a high concentration of antibody-linked reporters. However, this linearly increases the number of false positives due to low-level nonspecific binding of the reporters to a surface. For most immunoassays the limit of detection is capped by the ratio of false negatives to false positives, which is fixed across a range of antibody-reporter concentrations due to non-specific surface binding. Nanoswitch catenanes overcome this problem by using kinetic proofreading (see below) to drive false positives effectively to zero with only a minimal increase in false negatives. Furthermore, target-free- reporter destruction is done in solution phase, thus surface stickiness does not present a significant problem.

Kinetic proofreading (Hopfield J J, PNAS 71, 4135-4139, 1974) is a strategy for trading a modest increase in false negatives for a profound decrease in false positives. In the context of detection, the setup is a reaction in which a population of reporter complexes will undergo self-destruction with single-exponential decay for some specified duration of time, after which time the surviving ones will be permanently preserved. Reporters that bind the target analyte will self-destruct more slowly than those that do not bind the target analyte. As an example, consider the case of a target-bound reporter that has a lifetime of $\tau$ and a non-target-bound reporter that has a lifetime of $\tau/100$. In the case that this corresponded to a 100×stronger affinity, then any equilibrium-based detection would only be able to detect the target if it were present at ≥1% the total analytes. However, with kinetic proofreading, far better than equilibrium detection can be achieved, as illustrated in the table below.

Challenge Each Reporter to Maintain an Intact Antibody-Sandwich Bridge, which is Undergoing Single-Exponential Decay, for a User-Specified Duration between Mixing-Induced Breakage of Bridge 0 and Mixing-Induced Formation of Bridge 2 example parameters: $\kappa_{open(Ab\text{-}target\text{-}Ab)} = 1/\tau$, $\kappa_{open(Ab\text{-}non\text{-}target\text{-}Ab)} = 100\tau$

| user-specified duration (between triggered breakage of bridge 0 and triggered formation of bridge 2) | target survival $=\exp(-t/\tau)$ | non-target survival $=\exp(-100t/\tau)$ | target enrichment $=\exp(99t/\tau)$ |
|---|---|---|---|
| $0.1\tau$ | 0.91 | 4.5E−05 | 2E+04 |
| $0.25\tau$ | 0.78 | 1.4E−11 | 5.6E+10 |
| $0.5\tau$ | 0.61 | 1.9E−22 | 3.1E+21 |
| $\tau$ | 0.37 | 3.7E−44 | 9.9E+42 |
| $2\tau$ | 0.14 | 1.4E−87 | 9.8E+85 |

To achieve low false positives in the second stage, the reporter is designed to be composed of several weakly interacting components, such that when these components are diluted into bulk solution, the entropy cost to bringing them back together suppresses spontaneous reconstitution of the reporter down to zero. However, for an intact catenane representing a legitimate detection event, the various components are held together in high effective concentration, therefore reporter activation is achievable. An example of such a reporter system is shown in FIG. 2.

(2) Contamination can be contained for nanoswitch catenanes by forming validated reporter constructs in the same device used for collection of blood. Therefore the time for contamination is limited to the moments of time between blood collection and reporter validation in the same device, which will be on the order of minutes. The only subsequent contamination can come from other validated reporters; however, since reporters can be given unique barcode identifications, therefore the chance for contamination by the same barcode will be very low.

(3) One approach for small sample volumes is to use microfluidics. However, leaching of analytes to the surfaces of the microfluidic channels becomes a significant problem at the high surface-area-to-volume ratios involved. Nanoswitch catenanes solve this problem of leaching to surfaces by doing all reporter validation in solution phase with low surface area to volume.

One also has to correct for errors in volume collected. Nanoswitch catenanes solve this problem by multiplexed detection of multiple biomarkers within the same sample, thus the sample volume can be calibrated with respect to standard markers assayed simultaneously.

(4) Because false positives in the first second stage can be driven effectively to zero, therefore it is not difficult to achieve efficient target capture within minutes (by using a high concentration and large excess of nanoswitch catenanes). Nanoswitch catenane validation can be accomplished within minutes, and reporter amplification can be achieve within minutes. Therefore, the entire process, from mixing nanoswitch catenanes with blood sample, to analysis of amplified surviving reporters, can be completed with ten minutes, for example. High-throughput is achievable as well, as one can multiplex the detection and readout of the amplicons, as each amplicon can be assigned a nearly unique barcoded template sequence. Costs are be relatively low compared to standard ELISA assays, as relatively small amounts of reagents are required, at least in the case where the analyte volume is low (e.g., less than 1mL).

Example 3

To achieve zM limit of detection:

Step 0: Capture ~100% of analytes on subset of reporters (or else significant false negatives will result)

Step 1: Preserve ~100% of analyte-bound reporters (or else significant false negatives will result) and destroy exactly 100% of analyte-free reporters (or else significant false positives will result)

Step 2: Amplify exactly 100% of surviving reporters (or else significant false negatives will result) but amplify nothing else (or else significant false positives will result)

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, means "at least one."

Unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A nanoswitch catenane comprising:
   (a) a single-stranded nucleic acid comprising
      (i) a first terminal domain comprising a first functional group, a first binding partner, and a second functional group;
      (ii) a second terminal domain comprising a third functional group, a second binding partner, and a fourth functional group, wherein the first and second terminal domains are linked to form a host ring, wherein the first and fourth functional groups react in the presence of a reaction agent to form a link, wherein the first and second binding partners specifically bind to a biomolecule of interest to form a link, and wherein the second and third functional groups form a link that breaks in the presence of a dissociation agent; and
   (b) at least two circular nucleic acid guest rings catenated with the host ring.

2. The nanoswitch catenane of claim 1, wherein the at least two circular nucleic acid guest rings are single-stranded nucleic acids.

3. The nanoswitch catenane of claim 1, wherein the first binding partner is located between the first functional group and the second functional group, and wherein the second binding partner is located between the third functional group and the fourth functional group, and wherein the first and fourth functional groups are located at the distal end of the terminal domain.

4. The nanoswitch catenane of claim 1, wherein the link formed between the first and fourth functional groups is a covalent link.

5. The nanoswitch catenane of claim 1, wherein the link formed between the second and third functional groups is a covalent link.

6. The nanoswitch catenane of claim 1, wherein the link formed between the first and second binding partners is a non-covalent link.

7. The nanoswitch catenane of claim 1, wherein the single-stranded nucleic acid is a single-stranded deoxyribonucleic acid (DNA).

8. The nanoswitch catenane of claim 1, wherein the single-stranded nucleic acid has a length of 100 nucleotides to 1000 nucleotides.

9. The nanoswitch catenane of claim 1, wherein the first and/or second terminal domain has a length of 30 nucleotides to 100 nucleotides.

10. The nanoswitch catenane of claim 1, wherein one of the first or third functional groups is an azide, and wherein the other of the first or third functional groups is an alkyne.

11. The nanoswitch catenane of claim 1, wherein the first functional group is azide, and the second functional group is trans-cyclooctene (TCO).

12. The nanoswitch catenane of claim 1, wherein the first and second biomolecule binding partners are proteins.

13. The nanoswitch catenane of claim 1, wherein the first and second biomolecule binding partners are antibodies, aptamers, or nanobodies.

14. The nanoswitch catenane of claim 1, wherein the second and fourth functional groups are thiol groups.

15. The nanoswitch catenane of claim 1, wherein the catenane comprises at least 3 guest rings.

16. The nanoswitch catenane of claim 15, wherein the catenane comprises 3-20 guest rings.

17. The nanoswitch catenane of claim 1, wherein at least one of the at least two guest rings is linked to or encodes a component of an amplification reaction.

18. The nanoswitch catenane of claim 17, wherein the amplification reaction is a rolling-circle amplification reaction or a hybridization chain reaction.

19. A nanoswitch catenane comprising:
   (a) a single-stranded nucleic acid comprising a first and second terminal domain linked to each other to form a host ring by one of a first, second or third switchable bridges, wherein the first switchable bridge is formed in the presence of a reaction agent through the reaction of two cognate functional groups, each linked to a terminal domain of the single-stranded nucleic acid, wherein the second switchable bridge is formed in the presence of a biomolecule of interest through binding of the biomolecule of interest to two cognate antibodies, each linked to a terminal domain of the single stranded nucleic acid, and wherein the third switchable bridge is a link between two cognate functional groups that breaks in the presence of a dissociation agent; and
   (b) a circular nucleic acid guest ring catenated with the host ring.

20. A nanoswitch catenane comprising:
   (a) a single-stranded nucleic acid comprising
      (i) a first terminal domain comprising an azide, an antibody, and a thiol group, and
      (ii) a second terminal domain comprising an alkyne, an antibody, and a thiol group, wherein the antibody of (i) and the antibody of (ii) specifically bind to a biomolecule of interest; and
   (b) a circular nucleic acid guest ring catenated with a host ring.

21. The nanoswitch catenane of claim 20, wherein the azide and the alkyne are conjugated to form a covalent link.

22. The nanoswitch catenane of claim 20, wherein the antibody of (i) and the antibody of (ii) are bound to a biomolecule of interest to form a non-covalent link.

23. The nanoswitch catenane of claim 20, wherein the thiol groups are conjugated to form a covalent link.

24. A method of detecting a biomolecule of interest, comprising in the following ordered steps:
   (a) incubating a sample suspected of containing a biomolecule of interest with a nanoswitch catenane of claim 1 to permit binding of a biomolecule of interest to the first and second binding partners, thereby forming a reaction mixture;
   (b) incubating a dissociation reagent with the reaction mixture to break the link between the second and fourth functional groups of the nanoswitch catenane and to permit release of the guest ring from the host ring;
   (c) incubating the reaction mixture with a reaction agent to form a link between the first and third functional groups of the nanoswitch catenane; and
   (d) assaying the nanoswitch catenane for the presence or absence of the guest rings.

* * * * *

UNITED STATES PATENT AND TRADEMARK OFFICE
CERTIFICATE OF CORRECTION

PATENT NO. : 11,414,694 B2
APPLICATION NO. : 16/083932
DATED : August 16, 2022
INVENTOR(S) : Wesley Philip Wong et al.

It is certified that error appears in the above-identified patent and that said Letters Patent is hereby corrected as shown below:

In the Claims

In Claim 24, at Column 16, Line 27, the text:
"permit release of the guest ring from the host ring;"
Should be replaced with:
--permit release of the guest rings from the host ring;--.

Signed and Sealed this
Twelfth Day of March, 2024

Katherine Kelly Vidal
*Director of the United States Patent and Trademark Office*